United States Patent [19]

Pews

[11] Patent Number: 4,486,612
[45] Date of Patent: Dec. 4, 1984

[54] METHOD OF PREPARING TERTIARY CARBINOLS

[75] Inventor: R. Garth Pews, Midland, Mich.

[73] Assignee: The Dow Chemical Company, Midland, Mich.

[21] Appl. No.: 478,183

[22] Filed: Mar. 23, 1983

[51] Int. Cl.$^3$ .............................................. C07C 33/46
[52] U.S. Cl. .................................................... 568/812
[58] Field of Search ........................................ 568/812

[56] References Cited

U.S. PATENT DOCUMENTS

| | | | |
|---|---|---|---|
| 2,602,823 | 7/1952 | Ross | 568/812 |
| 2,606,213 | 8/1952 | Ladd | 568/812 |
| 2,975,211 | 3/1961 | Girard | 568/812 |
| 4,317,672 | 3/1982 | Griffith et al. | 568/812 |

FOREIGN PATENT DOCUMENTS

| | | | |
|---|---|---|---|
| 1275041 | 8/1968 | Fed. Rep. of Germany | 568/812 |
| 13699 | 6/1969 | Japan | 568/812 |

Primary Examiner—Werren B. Lone

[57] ABSTRACT

Tertiary carbinols are prepared by reacting an appropriate tertiary halide with water in the presence of a catalytic amount of an emulsifying agent. α-Methyl-α-(2,2,2-trichloroethyl)benzyl alcohol is prepared with a high rate of conversion and a low incidence of the formation of an olefin by-product. α-Methyl-α-(2,2,2-trichloroethyl)benzyl alcohol is useful as a nitrification inhibitor and as an intermediate in the preparation of structurally related nitrification inhibitors.

13 Claims, No Drawings

METHOD OF PREPARING TERTIARY CARBINOLS

BACKGROUND OF THE INVENTION

The present invention is directed to a method of preparing a tertiary carbinol from a tertiary halide in an aqueous reaction medium employing an emulsifying agent as a catalyst.

U.S. Pat. No. 4,317,672 discloses α-methyl-α-(2,2,2-trichloroethyl)benzyl alcohol and derivatives thereof as being nitrification inhibitors. This patent teaches a method of preparing α-methyl-α-(2,2,2-trichloroethyl)-benzyl alcohol by the reduction of α-(2,2,2-trichloroethyl)phenyl oxirane with lithium aluminum hydride.

SUMMARY OF THE INVENTION

In accordance with the present invention, a tertiary carbinol of the Formula I:

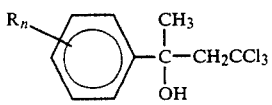

wherein n represents the integers 0, 1 or 2 and R represents $C_1$–$C_4$ alkyl, $C_1$–$C_4$ alkoxy, Cl, Br, F or I, is prepared by contacting a tertiary halide of the Formula II:

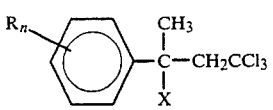

wherein X is Cl, Br or I and R and n are as defined above, with water in presence of an effective catalytic amount of an emulsifying agent having an HLB value of 10 or greater under conditions sufficient to cause the formation of the desired tertiary carbinol in a high yield. The tertiary carbinols produced by the present method are useful as nitrification inhibitors and as intermediates in the preparation of structurally related nitrification inhibitors.

Of particular interest in the practice of the present invention is a method of preparing α-methyl-α-(2,2,2-trichloroethyl)benzyl alcohol which is useful as a nitrification inhibitor and a chemical intermediate in the preparation of structurally related nitrification inhibitors. The present invention provides an advantage or producing low quantities of olefin by-products such as, for example, α-(2,2,2-trichloroethyl)styrene.

DETAILED DESCRIPTION OF THE INVENTION

When used herein the term "$C_1$–$C_4$" when used to describe alkyl and alkoxy groups indicates the number of carbon atoms that can be present in the respective group, i.e., 1, 2, 3 or 4 carbon atoms.

In the practice of the present invention it is essential to employ: a tertiary halide of Formula II above, water and a catalytic amount of an emulsifying agent.

The tertiary halides of Formula II above are known compounds and are prepared by halogenating an appropriate α-methylstyrene compound employing well known techniques. Preferably tertiary chlorides or tertiary bromides are employed as the starting materials. Most preferably, tertiary chlorides are employed as starting materials.

The employment of water as a reaction medium is the second critical component of the present invention. Usually about 5 or more parts by weight of water per part by weight of tertiary halide are employed as the reaction medium. While the exact amount of water employed is not critical, weight ratios of water:tertiary halide of 5:3 or less slow the rate of reaction and increase the amount of by-products produced. Preferably, from about 5 to about 10 parts by weight of water per part tertiary halide is employed in the present reaction.

The third essential component of the present invention is an emulsifying agent which acts as a catalyst. The emulsifying agent is present in an effective catalytic amount, usually at least about 0.01 or more percent by weight of the tertiary halide of Formula (II), and advantageously at least about 0.1 or more percent by weight. Preferably, the emulsifying agent is present between about 0.1 percent and 5 percent by weight of the tertiary halide, and even more preferably between about 0.5 to about 2 percent by weight. The term "effective catalytic amount", when used to describe the amount of emulsifier required in the present reaction, refers to an amount of emulsifier which, when added to the present reaction, accelerates the rate of the reaction in comparison to the present reaction conducted in the absence of an emulsifier.

Suitable emulsifying agents are those emulsifying agents or mixtures of emulsifying agents having an HLB (hydrophilic-lipophilic balance) value of 10 or greater and includes anionic, nonionic and cationic emulsifiers or surfactants. Suitable anionic emulsifiers include alkyl aryl sulfonates, such as, dodecyl benzene sulfonate, and alkyl/alkoxy sulfates, such as, lauryl alcohol sulfate. Suitable nonionic emulsifiers include polyoxyethylene alkyl phenols, such as, octylphenol ethoxylated with 9 moles of ethylene oxide which is commercially available as TRITON® X-100 emulsifier and alcohol ethoxylates, such as, lauryl alcohol plus 10 moles of ethylene oxide which is commercially available under a variety of trade names, such as, ALFONIC®, RENEX® 30 series, STANDAMUL® and SIPONIC®. Detergents which contain emulsifiers, such as TIDE® detergent, can also be used in the present reaction. Preferred emulsifiers include octyl phenol ethoxylated with 9 moles of ethylene oxide, commercially available as TRITON® X-100, and TIDE® detergent/emulsifier which contains a blend of dodecyl benzene sulfonate, lauryl alcohol sulfate and lauric diethanol amide emulsifiers.

The present hydrolysis reaction is advantageously conducted in the liquid phase at a temperature between about 15° C. and about 80° C., preferably between about 40° C. and about 60° C., and more preferably at a temperature of about 50° C. While the exact temperature is not critical, temperatures below about 30° C. require longer reaction times and temperatures above about 60° C. enhance the formation of undesired olefin by-products. The present reaction is typically conducted in the presence of agitation sufficient to maintain a thorough contacting of the reactants.

In conducting the present reaction neither the rate nor the order of the addition of reactants is critical. A typical reaction usually requires from about ½ to about 24 hours to be complete. The tertiary carbinol is recovered employing known separatory and purification techniques such as, for example, solvent extraction.

In a preferred embodiment of the present invention, an aqueous reaction mixture comprising about 100 parts by weight water, about 16 parts by weight α-methyl-α-(2,2,2-trichloroethyl)benzyl chloride and about 0.16 parts by weight TIDE ® brand detergent/emulsifier is mixed and heated to about 50° C. After about 4 hours at 50° C., the reaction is substantially complete. The desired α-methyl-α-(2,2,2-trichloroethyl)benzyl alcohol is recovered by extraction with carbon tetrachloride or ethyl acetate.

The following examples illustrate the practice of the present invention but should not be construed as limiting its scope. All percentages are by weight unless indicated otherwise.

EXAMPLE 1

Preparation of α-methyl-α-(2,2,2-trichloroethyl)benzyl chloride

Carbon tetrachloride (461.4 g, 3.0 mol), α-methylstyrene (118.2 g, 1.0 mol) and cuprous chloride (3.96 g, 0.02 mol) were placed in a 1 l three-necked flask equipped with magnetic stirrer, dropping funnel and reflux condenser. The solution was brought to a gentle reflux and cyclohexylamine (8 g, 0.08 mol) in 72 ml of carbon tetrachloride was added dropwise over a one hour period. After the initial addition, the heat was turned off and the reaction was sufficiently exothermic to maintain reflux until the addition was complete. The carbon tetrachloride solution was washed three times with 200 ml portions of 10% hydrochloric acid. After drying over MgSO$_4$ and evaporation of the carbon tetrachloride, the material was analyzed by standard nmr procedures and found to be about 95% pure α-methyl-α-(2,2,2-trichloroethyl)benzyl chloride. The major impurity was identified as α-(2,2,2-trichloroethyl)styrene.

EXAMPLE 2

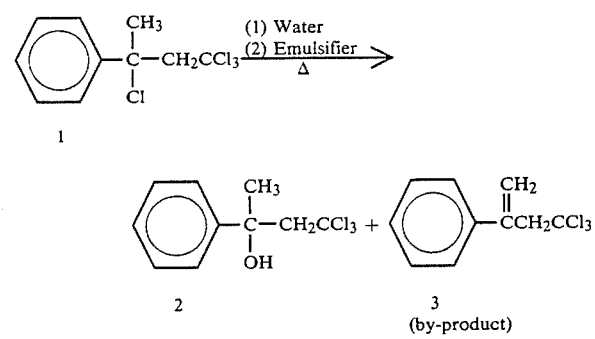

The experiments described in Table 1 were conducted in three-necked flasks equipped with mechanical stirrer, condenser and thermometer. Elevated temperatures were controlled by an I$^2$R Thermowatch L7-11008 heater. Product isolations were by extraction employing carbon tetrachloride or ethyl acetate as the extracting solvent.

TABLE 1

| Example Number | T (°C.) | H$_2$O (Gms) | 1 (Gms) | TIDE (Gms) | Time (Hrs) | Conversion | Recovery (Gms) | Analysis$^d$ 2 | 3 | 1 |
|---|---|---|---|---|---|---|---|---|---|---|
| 1 | R.T. | 150 | 16.4 | 0.16 | 16 | 87 | 14.75 | 74 | 13 | 13 |
| 2 | R.T. | 150 | 16.4 | 0.33 | 16 | 100 | —* | 91 | 9 | — |
| 3 | R.T. | 1500 | 164 | 3.3 | 16 | 100 | 130(86%)$^b$ | 93 | 7 | — |
| 4 | R.T. | 2250 | 246 | 4.9 | 16 | 85 | 210 | 77 | 8 | 15 |
| 5 | R.T. | 2250 | 246 | 4.9 | 48 | 100 | 290(91%)$^c$ | 93 | 7 | — |
| 6 | R.T. | 1250 | 260(95.5%) | 5.0 | 24 | 83 | — | 73 | 8 | 17 |
|   |   |   |   |   | 48 | 97 | — | 85 | 10 | 3 |
| 7 | 50° C. | 500 | 100 | 5 | 0 | 0 | — | 1.13 | 2.97 | 95.2 |
|   |   |   |   |   | 2 | 90.8 | — | 81.2 | 7.4 | 9.2 |
|   |   |   |   |   | 3 | 96.8 | — | 87.6 | 8.2 | 3.2 |
|   |   |   |   |   | 4 | 99.2 | — | 89.3 | 8.5 | 0.8 |
| 8 | 70° C. | 500 | 100 | 5 | 0 | — | — | 0.2 | 2.74 | 96.2 |
|   |   |   |   |   | 1 | — | — | 87 | 11 | 0.5 |
| 9 | 50° C. | 300 | 100 | 5 | 0 | — | — | 0.2 | 6.2 | 92.2 |
|   |   |   |   |   | 1 | — | — | 49.2 | 8.7 | 38.3 |
|   |   |   |   |   | 2 | — | — | 70.0 | 10.8 | 16.0 |
|   |   |   |   |   | 4 | — | — | 81.7 | 12.6 | 2.5 |
|   |   |   |   |   | 6.5 | — | — | 80.7 | 15.6 | 0.5 |

R.T. = room temperature
$^a$Assay Varies
$^b$After 2 Extractions
$^c$After 3 Extractions
$^d$Example Number 1–5 by nmr; Example Number 6–9 by Flame G.C.
*"—" denotes not calculated In similar operations, employing different tertiary halides and emulsifying agents in various concentrations under suitable conditions, described herein, substantially the same results are obtained, i.e., formation of the corresponding tertiary carbinol.

What is claimed is:

1. A method of preparing a tertiary carbinol of the Formula

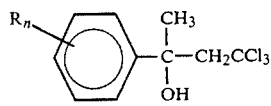

wherein n represents the integers 0, 1 or 2 and R represents $C_1$–$C_4$ alkyl, $C_1$–$C_4$ alkoxy, Cl, Br, F or I, the method comprising contacting a tertiary halide of the Formula,

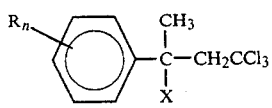

wherein X is Cl, Br or I and R and n are as defined above, with water in the presence of an effective catalytic amount of an emulsifying agent having an HLB value of 10 or greater and at a temperature between about 15° C. and about 80° C.

2. The method of claim 1 conducted at an elevated temperature and wherein X is Cl or Br.

3. The method of claim 2 wherein the emulsifying agent is TIDE ® brand detergent/emulsifier.

4. The method of claim 1 wherein the emulsifying agent is an alkyl aryl sulfonate, an alkyl/alkoxy sulfate, a polyoxyethylene alkyl phenol, an alcohol ethoxylate or mixtures thereof.

5. The method of claim 4 wherein the emulsifying agent is octylphenol ethoxylated with 9 moles of ethylene oxide.

6. A method of preparing α-methyl-α-(2,2,2-trichloroethyl)benzyl alcohol which comprises contacting from about 0.1 to about 50 parts by weight of α-methyl-α-(2,2,2-trichloroethyl)benzyl chloride with about 100 parts by weight of water in the presence of a catalytic amount of an emulsifying agent having an HLB value of 10 or greater at a temperature between about 15° C. and about 80° C. for a time sufficient to form the desired product.

7. The method of claim 6 wherein the emulsifying agent is TIDE ® brand detergent/emulsifier.

8. The method of claim 7 conducted at a temperature of about 50° C.

9. The method of claim 8 wherein from about 10 to about 20 parts by weight of α-methyl-α-(2,2,2-trichloroethyl)benzyl chloride are contacted with about 100 parts by weight of water.

10. The method of claim 9 wherein the emulsifying agent is present in the reaction in a concentration of between about 0.5 to about 2 percent by weight of α-methyl-α-(2,2,2-trichloroethyl)benzyl chloride.

11. The method of claim 6 wherein α-methyl-α-(2,2,2-trichloroethyl)benzyl bromide is substituted for α-methyl-α-(2,2,2-trichloroethyl)benzyl chloride.

12. The method of claim 6 wherein the emulsifying agent is an alkyl aryl sulfonate, an alkyl/alkoxy sulfate, a polyoxyethylene alkyl phenol, an alcohol ethoxylate or mixtures thereof.

13. The method of claim 6 wherein the emulsifying agent is octylphenol ethoxylated with 9 moles of ethylene oxide.

* * * * *